United States Patent [19]

Lee et al.

[11] Patent Number: 5,097,086

[45] Date of Patent: Mar. 17, 1992

[54] LIQUID CATALYST FOR OXIDATIVE COUPLING REACTIONS

[75] Inventors: Anthony L. Lee, Glen Ellyn; Robert F. Zabransky, Barrington Hills; Erek J. Erekson, LaGrange; S. Peter Barone, Hoffman Estates; Irvine J. Solomon, Highland Park, all of Ill.

[73] Assignee: Institute of Gas Technology, Chicago, Ill.

[21] Appl. No.: 708,460

[22] Filed: May 31, 1991

[51] Int. Cl.$^5$ .................... C07C 5/32; C07C 5/42; C07C 5/333; C07C 5/373

[52] U.S. Cl. .................... 585/379; 585/380; 585/400; 585/658; 585/660; 585/661

[58] Field of Search ............... 585/380, 400, 658, 660, 585/661, 379

[56] References Cited

U.S. PATENT DOCUMENTS

| | | | |
|---|---|---|---|
| 3,830,853 | 8/1974 | Khcheian et al. | 260/621 G |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,499,322 | 2/1985 | Jones et al. | 585/500 |
| 4,499,323 | 2/1985 | Gaffney | 585/500 |
| 4,499,324 | 2/1985 | Gaffney | 585/500 |
| 4,523,049 | 6/1985 | Jones et al. | 585/500 |
| 4,826,796 | 5/1989 | Erekson et al. | 502/202 |
| 4,956,327 | 9/1990 | Erekson et al. | 502/202 |

OTHER PUBLICATIONS

Keller, G. E. and M. M. Bhasin, J. of Catalysis 73, 9-19 (1982).

Hinsen, W. and M. Baerns, Chem.-Ztg., 107, 223-226 (1983).

Hinsen, W., W. Bytyn and M. Baerns, Proc. 8th Int. Congr. Catal., Berlin, III 581-592 (1984).

Kimble, James B. and John H. Kolts, "Oxidative Coupling of Methane to Higher Hydrocarbons", Energy Progress, vol. 6, p. 227 (1986).

Driscoll, D. J., W. M. Martir, J. Wang and J. H. Lunsford, J. Am. Chem. Soc. 107, 58-63 (1985).

Ito, T., J. Wang, C. Lin and J. H. Lunsford, J. Am. Chem. Soc. 107, 5062-5064 (1985).

Illingworth, G. F. and G. W. Lester, ACS Petroleum Division Preprints, 12, No. 3, 161 (1967).

Lee, K. W., M. J. Choi, S. B. Kim and C. S. Choi, Ind. Eng. Chem. Res. 26, 1951 (1987).

Kegeyan, E. M., I. S. Vardanyan and A. B. Nalbandyan, Kinetics and Catalysis 17, No. 4, 749-754 and No. 4, 755-759 (1976).

Chemical Abstracts 97:127153K (1982).

Chemical Abstracts 99:70137t (1983).

Chemical Abstracts 101:74734t (1984).

Chemical Abstracts 101:38205n (1984).

Kirk-Othmer, Encyclopedia of Chemical Technology, Third Edition, vol. 21, Styrene, pp. 770-801.

Ward, K. J. et al., Hydrocarbon Processing, vol. 66, No. 3, Mar. 1987, pp. 47-48.

Fiedorow, R., W. Przystajko, M. Sopa and I. G. Dalla Lana, The Nature and Catalytic Influence of Coke on Alumina: Oxidative Dehydrogenation of Ethylbenzene, Journal of Catalysis 68, pp. 33-41 (1981).

Vrieland, G. E., Oxydehydration of Ethylbenzene to Styrene Over Metal Phosphates, Journal of Catalysis 111, pp. 1-13 (1988).

Primary Examiner—Anthony McFarlane
Assistant Examiner—Nhat Phan
Attorney, Agent, or Firm—Speckman & Pauley

[57] ABSTRACT

A liquid catalyst composition for the oxidative coupling of methane and other hydrocarbon compounds to produce higher hydrocarbons and for the oxidative dehydrogenation of aliphatic and alicyclic hydrocarbon compounds, aliphatic and alicyclic substituted aromatic hydrocarbons, and mixtures thereof is disclosed.

8 Claims, No Drawings

LIQUID CATALYST FOR OXIDATIVE COUPLING REACTIONS

BACKGROUND OF THE INVENTION

1. Field of the Invention

This invention relates to a liquid catalyst composition for production of higher hydrocarbons by oxidative coupling of methane, production of higher hydrocarbons by oxidative coupling of aliphatic and alicyclic hydrocarbon compounds with aliphatic and alicyclic substituted aromatic hydrocarbon compounds to form a longer substituent hydrocarbon on the aromatic ring, and production of unsaturated aliphatic and alicyclic chains by dehydrogenation of aliphatic and alicyclic compounds and aliphatic and alicyclic substituted aromatic hydrocarbon compounds. Reactions of hydrocarbons with oxygen in the presence of a liquid catalyst composition of this invention result in high conversion of the hydrocarbons with high selectivity for olefins.

2. Description of the Prior Art

Methane is currently available in large quantities from natural gas, anaerobic digestion of organic material, and chemical processing sources. However, use of methane as a chemical feedstock has been limited due to its high stability. It has been highly desirable to develop a catalyst for such reactions to enable operation under milder conditions with greater control over thermodynamic and kinetic processes as well as provide product selectivity and high reaction rate.

Oxidative coupling of methane to form higher hydrocarbons has been shown to be effected over a number of metal oxides, but yields of desired products have been low, as discussed by Keller, G.E. and M.M. Bhasin, J. of Catalysis 73, 9-19 (1982). Sodium and lead on alumina has been found to catalyze the formation of ethane and ethylene from methane, as disclosed in Hinsen, W. and M. Baerns, Chem.-Ztg., 107, 223-226 (1983) and Hinsen, W., W. Bytyn and M. Baerns, Proc. 8th Int. Congr. Catal., Berlin, III 581-592 (1984). Several U.S. patents teach a series of supported metal oxides which while effective for the conversion of methane to ethane and ethylene, are based on reducible metal oxides and used in a stoichiometric fashion by alternately exposing them to an oxidizing atmosphere and then to methane in the absence of oxygen. U.S. Pat. Nos. 4,443,644; 4,443,645; 4,443,646; 4,443,647; 4,443,648; 4,443,649; 4,444,984, 4,499,322; 4,499,323; 4,499,324; and 4,523,049.

Later work has demonstrated that magnesium oxide and calcium oxide, when promoted with alkali metal salts, are active for oxidative coupling of methane to ethane and ethylene in the presence of oxygen. See Kimble, James B. and John H. Kolts, "Oxidative Coupling of Methane to Higher Hydrocarbons", Energy Progress, Vol. 6, p. 227 (1986); Driscoll, D.J., W.M. Martir, J. Wang and J.H. Lunsford, J. Am. Chem. Soc. 107, 58-63 (1985); and Ito, T., J. Wang, C. Lin and J.H. Lunsford, J. Am. Chem. Soc. 107, 5062-64 (1985). These later catalysts have the advantage of operating continuously, not requiring regeneration or pretreatment.

Borates and boron compounds have been used in partial oxidation of hydrocarbons, such as boric acid to oxidize long chain normal paraffins in the liquid phase (Illingworth, G.F. and G.W. Lester, ACS Petroleum Division Preprints, 12, No. 3, 161 (1967)) and oxidation of n-dodecane in the liquid phase to the corresponding alcohol (Lee, K.W., M.J. Choi, S.B. Kim and C.S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E.M., I.S. Vardanyan and A.B. Nalbandyan, Kinetics and Catalysis 17, No. 4, 749-754 and No. 4, 755-759 (1976))

A number of publications describe oxidative methylation of toluene performed in Russia: Chemical Abstracts 97:127153K (1982) teaches non-catalytic methylation of toluene depended mostly on pressure and $PhMe/O/CH_4$ molar ratio; Chemical Abstracts 99:70137t (1983) teaches oxidative methylation of toluene using a Ni-V oxide or V oxide catalyst; Chemical Abstracts 101:74734t (1984) teaches oxidative methylation of toluene in presence of oxygen (max. 15 percent in reaction mixture) results in products including styrene; Chemical Abstracts 101:38205 n (1984) teaches simultaneous production of styrene, ethylbenzene, benzene, and phenols by reaction of toluene with $C_{1-4}$ alkanes in the presence of oxygen and $Fe_2O_3$ or $TiO_2$ at 600-800°. Productivity increased at higher pressure in presence of $H_2O_2$ and/or $(Me_3C)_2O_2$; and U.S. Pat. No. 3,830,853 teaches reaction of toluene with a lower paraffin space velocity of 2000-10000 $hour^{-1}$.

Styrene is an important commercial unsaturated aromatic monomer used extensively in the manufacture of plastics by polymerization and copolymerization. On a commercial scale, the great majority of the world's styrene is produced by dehydrogenation of ethylbenzene. A review of styrene synthesis processes is given in Kirk-Othmer, Encyclopedia of Chemical Technology, Third Edition, Vol. 21, Styrene, pgs. 770-801. One commercial process for production of styrene is the UOP Styro-Plus process using ethylbenzene and superheated steam under vacuum for the catalytic dehydrogenation of ethylbenzene as taught by Ward, D.J. et al, Hydrocarbon Processing, Vol. 66, No. 3, March 1987, pgs 47-48. Use of coke-covered alumina and boron-/alumina catalysts for oxidative dehydrogenation of ethylbenzene is taught by Fiedorow, R., W. Przystajko, M. Sopa and I.G. Dalla Lana, The Nature and Catalytic Influence of Coke on Alumina: Oxidative Dehydrogenation of Ethylbenzene, Journal of Catalysis 68, pgs. 33-41 (1981). Oxidative dehydrogenation of ethylbenzene to styrene over metal pyrophosphates, such as cerium, tin, zirconium, and titanium phosphates and calcium magnesium, strontium, barium, nickel, aluminum, thorium, zinc and silicon phosphates is taught by Vrieland, G.E., Oxydehydration of Ethylbenzene to Styrene over Metal Phosphates, Journal of Catalysis 111, pgs. 1-13 (1988). This article teaches the condensed phosphate surface is the dominant factor as a catalyst and that the cation has little or no effect.

Oxidative coupling reactions conducted in the presence of solid catalysts are known, the light-off temperature usually being higher than 600° C. and the upper temperature limit being about 850° C., above which carbon dioxide becomes the major product. Consequently, the operating temperature range is limited to about 250° C. which, in turn, limits the desired product yield to less than about 30%. Such catalysts are disclosed in U.S. Pat. No. 4,826,796 and U.S. Pat. No. 4,956,327.

It is highly desirable to develop a catalyst which enables such reactions to be carried out under milder conditions with greater control over thermodynamic and kinetic processes as well as provide product selectivity and higher reaction rates.

SUMMARY OF THE INVENTION

This invention provides a suitable liquid catalyst composition and process for oxidative coupling of hydrocarbons to produce higher molecular weight hydrocarbons utilizing said liquid catalyst composition. The reaction of hydrocarbons with oxygen is conducted in the presence of a liquid catalyst composition at temperatures below the temperatures required for such reactions using solid catalysts, resulting in high conversion of hydrocarbons with a high selectivity for olefins. The liquid catalyst composition of this invention is a salt of known elements used in known solid catalysts dissolved in aqueous solutions. More specifically, the liquid catalyst composition of this invention is a salt selected from the group consisting of sulfates, halides, nitrates, carbonates, carboxylates and phosphates of active elements selected from the group cobalt, vanadium, copper, manganese, palladium, and chromium.

In a preferred embodiment of this invention, a promoted liquid catalyst composition of the liquid catalyst composition as described above includes salts of promoter elements selected from the group consisting of lithium, sodium, potassium, strontium, calcium, magnesium, and boron, also dissolved in an aqueous solution.

This invention provides a liquid catalyst composition for oxidative coupling of methane to produce a higher molecular weight hydrocarbon and for oxidative coupling of aliphatic and alicyclic hydrocarbon compounds with aliphatic and alicyclic substituted aromatic hydrocarbon compounds to produce a longer substituent hydrocarbon on the aromatic ring. The reaction of an aliphatic or alicyclic hydrocarbon compound with methane is conducted in the presence of the liquid catalyst composition at elevated temperature according to the following general reaction:

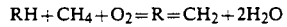

where R is an aliphatic or alicyclic hydrocarbon radical. The reaction of an aliphatic or alicyclic hydrocarbon compound with an aliphatic or alicyclic substituted aromatic hydrocarbon compound and oxygen is conducted in the presence of the liquid catalyst composition at elevated temperature according to the following general reaction:

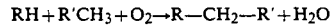

where R is an aliphatic or alicyclic hydrocarbon radical and R' is an aliphatic or alicyclic hydrocarbon radical substituted on an aromatic hydrocarbon ring.

It is unexpected that liquid catalyst compositions active for oxidative coupling as described above involving carbon-carbon bond formation would also be active for dehydrogenation involving carbon-hydrogen bond breaking with subsequent carbon-carbon double bond formation. Dehydrogenation of saturated organics has been described by Thomas, Charles L., Catalytic Processes and Proven Catalysts, Chap. 6, Dehydrogenation, pp. 41-45, Academic Press (1970).

This invention provides a liquid catalyst composition and process for oxidative dehydrogenation of aliphatic and alicyclic hydrocarbon compounds and of aliphatic and alicyclic chains of aliphatic and alicyclic substituted aromatic hydrocarbon compounds to produce an unsaturation in the hydrocarbon chain. The reaction of an aliphatic or alicyclic hydrocarbon compound, an aliphatic or alicyclic substituted aromatic hydrocarbon compound and mixtures thereof in the dehydrogenation reaction is conducted in the presence of a liquid catalyst composition at elevated temperature. The oxidative dehydrogenation may proceed according to the following general reaction wherein C—C bonding in a compound RH or R'CH$_3$ +1/2O$_2$ is converted to C=C bonding + H$_2$O, wherein R is an aliphatic or alicyclic hydrocarbon radical having 2 and more carbon atoms; and R' is an aliphatic or alicyclic hydrocarbon radical substituted on an aromatic hydrocarbon ring. In the case of dehydrogenation of ethylbenzene to styrene according to this invention partial oxidation or oxidative dehydrogenation proceeds according to the general reaction:

DESCRIPTION OF PREFERRED EMBODIMENTS

The liquid catalyst composition of this invention and the liquid catalyst composition used in the oxidative coupling of hydrocarbons in accordance with the process of this invention is an aqueous solution of the salts of a catalytically active metal, preferably cobalt, vanadium, copper, manganese, palladium, chromium and mixtures thereof. Preferred salts are nitrates, halides, sulfates, carbonates, carboxylates, phosphates, acetates and mixtures thereof. In a particularly preferred embodiment, the catalytically active metal comprises between about 0.1 to about 15.0 per cent by weight of the liquid catalyst composition.

In another preferred embodiment of this invention, the liquid catalyst composition of this invention comprises aqueous solutions of the salts of catalytically active metals combined with salts of promoter elements. The preferred promoter elements are lithium, sodium, potassium, strontium, calcium, magnesium, boron, and mixtures thereof. Preferred salts are nitrates, halides, sulfates, carbonates, carboxylates, phosphates, acetates and mixtures thereof. In a particularly preferred embodiment, the promoter element comprises between about 0.0001 to about 1.0 per cent by weight of the liquid catalyst composition.

The liquid catalyst composition of this invention provides oxidative coupling of hydrocarbons and oxygen bubbled through or otherwise brought into contact with the liquid catalyst composition, such as a mixture of cobalt nitrate and copper nitrate dissolved in water. Feedstock comprising methane, light alkanes - primarily C$_2$-C$_6$, alicyclic hydrocarbons, and aromatic hydrocarbons and not containing any interfering compounds are suitable for use in the process of this invention. Likewise, any oxygen containing gas not containing interfering chemical compounds is useful as feedstock in this invention. The term "oxygen containing gases" as used throughout this disclosure and claims means gas containing oxygen, such as air or steam, and gases having an oxygen content of up to 100%. For oxidative coupling of methane, for example, it is preferred to use oxygen containing gas comprising over 5 volume percent oxygen. The mole ratio of oxygen to methane in the gas mixture subjected to the process of this invention is about 0.1 to about 1.5 and preferably about 0.5 to about 1.0.

The catalyst of this invention provides a longer hydrocarbon substituent on an aromatic ring by gas phase oxidative coupling of saturated carbon atoms of an aliphatic or alicyclic hydrocarbon compound with an aliphatic or alicyclic substituted aromatic hydrocarbon and oxygen. Suitable aliphatic and alicyclic hydrocarbon compounds for use as feedstocks in the process of this invention include straight and branched chain saturated and unsaturated aliphatic hydrocarbons, such as methane, ethane, propane, butane, heptane, pentane, hexane, octane, isobutane, isohexane, isooctane, 1-pentene, 1-hexene and mixtures thereof; cyclic chain saturated and unsaturated alicyclic hydrocarbons, such as cyclobutane, cycloheptane, cycloheptene, cyclohexane, cyclohexene and mixtures thereof; and aryl substituted aliphatic and alicyclic hydrocarbons, such as toluene, xylene, mesitylene, durene, cumene and mixtures thereof. In the case of unsaturated hydrocarbons, it should be noted that the oxidative coupling of this invention does not occur at the unsaturated bonding. Suitable aliphatic and alicyclic substituted aromatic hydrocarbon compounds for use as feedstocks in this invention are aromatic ring hydrocarbons having at least one aliphatic or alicyclic hydrocarbon radical substituent on the aromatic ring, such as toluene, xylene, indan, tetralin, and mixtures thereof.

The liquid catalyst composition may be placed into a reactor, such as a sparged stirred tank reactor, or other reactor type known to the art. Suitable reactor vessels for use at the desired operating temperatures and pressures are well known to those skilled in the art. The oxidative coupling of hydrocarbons to form olefins in accordance with the process of this invention is carried out by bubbling the hydrocarbons and oxygen through the liquid catalyst composition bed at a space velocity of about 100 to about 3000 vol/vol/hr providing gas residence times of about 0.01 to about 0.0003 hour. Suitable temperatures are about 125° C. to about 500° C., preferably between about 150° C. and about 250° C. The reactions may be carried out at pressures of about 50 psig to about 900 psig, preferably about 500 psig to about 800 psig. To minimize loss of the liquid catalyst composition, the reactor is equipped with a reflux column so that evaporated liquid catalyst composition is condensed and returned to the reactor.

The catalyst of this invention provides unsaturated aliphatic and alicyclic chains by oxidative dehydrogenation of saturated carbon atoms of an aliphatic or alicyclic hydrocarbon compound and an aliphatic or alicyclic substituted aromatic hydrocarbon and mixtures thereof. Suitable aliphatic and alicyclic hydrocarbon compounds for use as feedstocks in the process of this invention include straight and branched chain saturated aliphatic hydrocarbons, such as ethane, propane, butane, heptane, pentane, hexane, octane, isobutane, isohexane, isooctane, and mixtures thereof; and cyclic chain saturated hydrocarbons, such as cyclobutane, cycloheptane, cyclohexane, and mixtures thereof. Suitable aliphatic and alicyclic substituted aromatic hydrocarbon compounds for use as feedstocks in this invention are aromatic ring hydrocarbons having at least one saturated aliphatic or alicyclic hydrocarbon radical substituent on the aromatic ring, such as ethylbenzene, indan, tetralin and mixtures thereof.

For oxidative dehydrogenation in accordance with the process of this invention, the hydrocarbon reactant is brought into contact in a reactor with the liquid catalyst composition defined above. Oxygen may be added up to a mole amount of about 2.0 moles oxygen per mole of hydrocarbon, preferably about 0.5 to about 1.5 moles oxygen per mole of hydrocarbon. The gaseous aliphatic or alicyclic hydrocarbon or aromatic feedstock is charged to a reactor containing the liquid catalyst composition and pressurized with air to between about 50 psig to about 900 psig, preferably between about 500 psig to about 800 psig. Suitable temperatures in the reactor are about 125° C. to about 500° C., preferably about 150° C. to about 250° C. Residence time of the hydrocarbons within the reactor is about 1 second to about 3600 seconds, preferably about 2000 seconds to about 3600 seconds.

One important dehydrogenation reaction according to the process of this invention is the production of styrene by oxidative dehydrogenation of ethylbenzene in the presence of the above defined liquid catalyst composition according to the reactions set forth above. At 727° C. the heat of reaction ( H) for oxidative dehydrogenation is —29.4 kcal/mole exothermic and the sensible heat plus the heat of vaporization of ethylbenzene is about 33.0 kcal/mole. Thus the oxidative dehydrogenation process operates close to autothermal conditions after initial light-off. Conventional processes for production of styrene from ethylbenzene feedstock require large amounts of superheated steam (800° C. and molar ratio 1 steam to 1 ethylbenzene) because the conversion of ethylbenzene to styrene is endothermic. The dehydrogenation process of this invention uses a single reactor in a process that does not require superheated steam.

The following specific examples are set forth in detail to illustrate the invention and should not be considered to limit the invention in any manner.

EXAMPLE I

An autoclave was charged with a liquid catalyst composition in accordance with this invention comprising deionized water, cobalt nitrate, and copper nitrate, and ethylbenzene, the ethylbenzene having been bubbled through the liquid catalyst composition. The gas phase above the liquid was charged to 500 psig with a mixture of methane and air. The autoclave was stirred and heated to 225° C. The major product was benzaldehyde, a partial oxidation product of ethylbenzene. Also produced were small amounts of styrene. All of the ethylbenzene was consumed.

EXAMPLE II

A liquid catalyst composition in accordance with this invention was prepared by dissolving 16.11 grams of cobalt sulfate heptahydrate ($CoSC_4-7H_2O$) in 200.02 grams of deionized water.

The cobalt sulfate solution and 33.23 grams (0.31299 gram-moles) of ethylbenzene were charged into a 1 liter autoclave. The autoclave was pressurized with air up to 500 psig and closed off. The reactor was heated to 175° C. and held within 5 degrees of that temperature for 1 hour while stirring. The reactor was cooled to ambient temperature. Upon depressurization of the reactor, the gas was measured at 0.53 standard cubic feet containing 2.88% $CO_2$ and CO. The liquids, both organic and aqueous, were analyzed for products. The products obtained are shown in Table I:

TABLE I

| | |
|---|---|
| Ethylbenzene | .29619 gm-moles |
| Benzene | .00214 gm-moles |
| Toluene | .00043 gm-moles |
| Xylenes | .00022 gm-moles |
| Styrene | .00435 gm-moles |
| Benzaldehyde | .00466 gm-moles |
| Benzoic Acid | .00428 gm-moles |
| Acetophenone | .00071 gm-moles |

The overall conversion of ethylbenzene was 5.4%. The selectivity to styrene was 25.92%.

EXAMPLE III

In a similar manner, the liquid catalyst composition in accordance with this invention was prepared by dissolving 9.09 grams of copper sulfate (anhydrous) in 200.44 grams of deionized water.

The copper sulfate solution, 33.50 grams (.31553 gram-moles) of ethylbenzene, and 13.37 grams of nitrobenzene were charged into a 1 liter autoclave. The autoclave was pressurized with air up to 500 psig and closed off. The reactor was heated to 175° C. and held within 5 degrees of that temperature for 1 hour while stirring. The reactor was cooled to ambient temperature. Upon depressurization of the reactor, the gas was measured at 0.59 standard cubic feet containing $CO_2$ and CO. The liquids, both organic and aqueous, were analyzed for products. The products obtained are shown in Table II.

TABLE II

| | |
|---|---|
| Ethylbenzene | .29773 gm-moles |
| Benzene | .00329 gm-moles |
| Toluene | .00166 gm-moles |
| Xylenes | .00003 gm-moles |
| Styrene | .00719 gm-moles |
| Benzaldehyde | .00697 gm-moles |
| Benzoic Acid | .00263 gm-moles |
| Acetophenone | .01653 gm-moles |
| Nitrobenzene | .08473 gm-moles |

The overall conversion of ethylbenzene was 4.5%. The selectivity to styrene was 18.75%.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of th invention.

We claim:

1. A process for producing unsaturated aliphatic and alicyclic hydrocarbon chains by oxidative dehydrogenation, said process comprising:
   dehydrogenating a compound selected from the group consisting of aliphatic hydrocarbon compounds, alicyclic hydrocarbon compounds, aliphatic substituted aromatic hydrocarbon compounds, alicyclic substituted aromatic hydrocarbon compounds, and mixtures thereof in the presence of oxygen and an aqueous catalyst composition comprising a salt of an active metal selected from the group consisting of cobalt, vanadium, copper, manganese, palladium, chromium, and mixtures thereof, said active metal comprising between about 0.1 to about 15.0 percent by weight of said aqueous catalyst composition, dissolved in an aqueous solution, said salt selected from the group consisting of nitrates, halides, sulfates, carbonates, carboxylates, phosphates, acetates and mixtures thereof.

2. A process according to claim 1 wherein said aliphatic substituted aromatic hydrocarbon compound is ethylbenzene.

3. A process according to claim 1 wherein said aliphatic hydrocarbon compounds are selected from the group consisting of ethane, propane, butane, heptane, pentane, hexane, octane, isobutane, isohexane, isooctane, and mixtures thereof, said alicyclic hydrocarbon compounds are selected from the group consisting of cyclobutane, cycloheptane, cyclohexane, and mixtures thereof, said aliphatic substituted aromatic hydrocarbon compound is ethylbenzene and said alicyclic substituted aromatic hydrocarbon compounds are selected from the group consisting of indan, tetralin and mixtures thereof.

4. A process according to claim 1 wherein said process is carried out at a temperature of about 125° C. to about 500° C.

5. A process for producing unsaturated aliphatic and alicyclic hydrocarbon chains by oxidative dehydrogenation, said process comprising:
   dehydrogenating a compound selected from the group consisting of aliphatic hydrocarbon compounds, alicyclic hydrocarbon compounds, aliphatic substituted aromatic hydrocarbon compounds, alicyclic substituted aromatic hydrocarbon compounds, and mixtures thereof in the presence of oxygen and a promoted aqueous catalyst composition comprising a metal salt of an active metal selected from the group consisting of cobalt, vanadium, copper, manganese, palladium, chromium, and mixtures thereof, said active metal comprising between about 0.1 to about 15.0 percent by weight of said promoted aqueous catalyst composition and a promoter salt of a promoter element selected from the group consisting of lithium, sodium, potassium, strontium, calcium, magnesium, boron, and mixtures thereof, said promoter element comprising between about 0.0001 to about 1.0 percent by weight of said promoted aqueous catalyst composition, said metal salt and said promoter salt being dissolved in an aqueous solution, said metal salt and said promoter salt selected from the group consisting of nitrates, halides, sulfates, carbonates, carboxylates, phosphates, acetates, and mixtures thereof.

6. A process according to claim 5 wherein said aliphatic substituted aromatic hydrocarbon compound is ethylbenzene.

7. A process according to claim 5 wherein said aliphatic hydrocarbon compounds are selected from the group consisting of ethane, propane, butane, heptane, pentane, hexane, octane, isobutane, isohexane, isooctane, and mixtures thereof, said alicyclic hydrocarbon compounds are selected from the group consisting of cyclobutane, cycloheptane, cyclohexane, and mixtures thereof, said aliphatic substituted aromatic hydrocarbon compound is ethylbenzene and said alicyclic substituted aromatic hydrocarbon compounds are selected from from the group consisting of indan, tetralin and mixtures thereof.

8. A process according to claim 5 wherein said process is carried out at a temperature of about 125° C. to about 500° C.

* * * * *